US007605172B2

(12) United States Patent
Commons

(10) Patent No.: US 7,605,172 B2
(45) Date of Patent: Oct. 20, 2009

(54) THIAZOLO-NAPHTHYL ACIDS

(75) Inventor: Thomas J. Commons, Wayne, PA (US)

(73) Assignee: Wyeth, Madison, NJ (US)

( * ) Notice: Subject to any disclaimer, the term of this patent is extended or adjusted under 35 U.S.C. 154(b) by 513 days.

(21) Appl. No.: 11/208,772

(22) Filed: Aug. 22, 2005

(65) Prior Publication Data
US 2006/0052420 A1 Mar. 9, 2006

Related U.S. Application Data

(60) Provisional application No. 60/603,739, filed on Aug. 23, 2004.

(51) Int. Cl.
A61K 31/44 (2006.01)
C07D 277/20 (2006.01)
A01N 43/78 (2006.01)

(52) U.S. Cl. .................. 514/340; 514/365; 548/202

(58) Field of Classification Search .................. None
See application file for complete search history.

(56) References Cited

U.S. PATENT DOCUMENTS

| 3,026,325 | A | 3/1962 | Heinzelman et al. ......... 548/496 |
| 3,476,770 | A | 11/1969 | Scherrer ...................... 548/494 |
| 3,557,142 | A | 1/1971 | Bell ............................ 548/516 |
| 3,843,683 | A | 10/1974 | Bell ............................ 548/493 |
| 4,478,819 | A | 10/1984 | Hercelin et al. ............. 424/457 |
| 4,736,043 | A | 4/1988 | Michel et al. ............... 548/492 |
| 4,851,406 | A | 7/1989 | Martens et al. ......... 514/217.04 |
| 5,164,372 | A | 11/1992 | Matsuo et al. ................ 514/19 |
| 5,234,917 | A | 8/1993 | Finkelstein et al. ......... 514/397 |
| 5,420,289 | A | 5/1995 | Musser et al. ............... 548/159 |
| 5,482,960 | A | 1/1996 | Berryman .................... 514/414 |
| 5,502,187 | A | 3/1996 | Ayer et al. ................... 544/117 |
| 5,532,276 | A | 7/1996 | Mederski et al. ............ 514/303 |
| 5,541,343 | A | 7/1996 | Himmelsbach et al. ..... 514/424 |
| 5,562,859 | A | 10/1996 | Schlosser et al. ....... 252/299.61 |
| 5,612,360 | A | 3/1997 | Boyd et al. .................. 514/381 |
| 5,693,637 | A | 12/1997 | Klinge et al. ............... 514/221 |
| 5,859,044 | A | 1/1999 | Dow et al. ................... 514/419 |
| 6,048,875 | A | 4/2000 | De Nanteuil et al. ........ 514/314 |
| 6,110,963 | A | 8/2000 | Malamas .................... 514/443 |
| 6,137,002 | A | 10/2000 | Fisher et al. ................ 562/440 |
| 6,166,069 | A | 12/2000 | Malamas et al. ............ 514/469 |
| 6,232,322 | B1 | 5/2001 | Malamas et al. ............ 514/303 |
| 6,251,936 | B1 | 6/2001 | Wrobel et al. .............. 514/443 |
| 6,302,837 | B1 | 10/2001 | De Nanteuil et al. ........ 514/337 |
| 6,479,524 | B1 | 11/2002 | Priepke et al. .............. 514/352 |
| 6,586,453 | B2 | 7/2003 | Dhanoa et al. ............. 514/365 |
| 6,599,929 | B2 | 7/2003 | Cho et al. .................. 514/415 |
| 6,787,556 | B1 | 9/2004 | Hargreaves et al. ......... 514/311 |
| 6,800,645 | B1 | 10/2004 | Cox et al. ................... 514/314 |
| 6,800,654 | B2 | 10/2004 | Mayer et al. ................ 514/381 |
| 6,844,358 | B2 | 1/2005 | Malamas et al. ............ 514/336 |
| 2003/0013732 | A1 | 1/2003 | Elokdah ..................... 514/301 |
| 2003/0018067 | A1 | 1/2003 | Elokdah et al. ............. 514/469 |
| 2003/0060497 | A1 | 3/2003 | Gerlach et al. .............. 514/414 |
| 2003/0125371 | A1 | 7/2003 | Elokdah et al. ............. 514/419 |
| 2004/0116488 | A1 | 6/2004 | Jennings et al. ............. 514/374 |
| 2004/0116504 | A1 | 6/2004 | Elokdah et al. ............. 514/419 |
| 2004/0122070 | A1 | 6/2004 | Jennings .................... 514/374 |
| 2004/0138283 | A1 | 7/2004 | Jennings et al. ............. 514/414 |
| 2004/0204417 | A1 | 10/2004 | Perez et al. ................. 514/249 |
| 2005/0070584 | A1 | 3/2005 | Havran et al. .............. 514/357 |
| 2005/0070585 | A1 | 3/2005 | Elokdah et al. ............. 514/364 |
| 2005/0070587 | A1 | 3/2005 | Elokdah et al. ............. 514/381 |
| 2005/0070592 | A1 | 3/2005 | Gundersen ................. 514/415 |
| 2005/0096377 | A1 | 5/2005 | Hu ............................. 514/419 |
| 2005/0113428 | A1 | 5/2005 | Gopalsamy et al. ......... 514/364 |
| 2005/0113436 | A1 | 5/2005 | Elokdah et al. ............. 514/411 |
| 2005/0113438 | A1 | 5/2005 | Hu et al. .................... 514/414 |
| 2005/0113439 | A1 | 5/2005 | Hu ............................. 514/414 |
| 2005/0119296 | A1 | 6/2005 | Elokdah et al. ............. 514/300 |
| 2005/0119326 | A1 | 6/2005 | Havran et al. .............. 514/414 |
| 2005/0119327 | A1 | 6/2005 | Hu ............................. 514/414 |
| 2005/0215626 | A1 | 9/2005 | Havran et al. .............. 514/469 |
| 2006/0020003 | A1 | 1/2006 | Commons et al. .......... 514/374 |
| 2006/0052348 | A1 | 3/2006 | Commons et al. ............ 514/92 |
| 2006/0052349 | A1 | 3/2006 | Commons et al. ............ 514/95 |

FOREIGN PATENT DOCUMENTS

| DE | 3147276 A1 | 6/1983 |
| DE | 43 38 770 A1 | 5/1995 |
| DE | 4341453 A1 | 6/1995 |

(Continued)

OTHER PUBLICATIONS

Chawla et al., "Challenges in Polymorphism of Pharmaceuticals", CRIPS vol. 5, No. 1, Jan.-Mar. 2004 (4 Pages).*

(Continued)

Primary Examiner—Golam M. M. Shameem
Assistant Examiner—Sun Jae Y Loewe
(74) Attorney, Agent, or Firm—Mabel Ng; Scott Larsen; David Kurlandsky

(57) ABSTRACT

The present invention relates to thiazolo-naphthyl acids of the formula

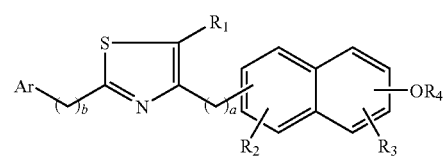

and methods of using them to modulate PAI-1 expression and to treat PAI-1 related disorders.

19 Claims, No Drawings

FOREIGN PATENT DOCUMENTS

| | | |
|---|---|---|
| DE | 4341665 A1 | 6/1995 |
| DE | 19537548 A1 | 4/1997 |
| DE | 19543639 A1 | 5/1997 |
| DE | 19753522 | 6/1999 |
| EP | 0 416 609 A2 | 3/1991 |
| EP | 0 445 811 A2 | 9/1991 |
| EP | 0 505 111 A2 | 9/1992 |
| EP | 0 508 723 A1 | 10/1992 |
| EP | 0 512 570 A1 | 11/1992 |
| EP | 0 512 675 A1 | 11/1992 |
| EP | 0 540 956 A1 | 5/1993 |
| EP | 0 560 407 A1 | 9/1993 |
| EP | 0 655 439 A2 | 5/1995 |
| EP | 0 658 553 A1 | 6/1995 |
| EP | 0 720 982 A1 | 7/1996 |
| EP | 0 740 937 A2 | 11/1996 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| JP | 63139172 A2 | 6/1988 |
| JP | 2004-250400 | 9/2004 |
| JP | 2004-250401 | 9/2004 |
| WO | 91/00277 A1 | 1/1991 |
| WO | 93/10114 A1 | 5/1993 |
| WO | 94/00120 A1 | 1/1994 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/19469 A1 | 6/1996 |
| WO | 96/21656 A1 | 7/1996 |
| WO | 96/26207 A1 | 8/1996 |
| WO | 96/32379 A1 | 10/1996 |
| WO | 97/04774 A1 | 2/1997 |
| WO | 97/09308 A1 | 3/1997 |
| WO | 97/28159 A1 | 8/1997 |
| WO | 97/43260 A1 | 11/1997 |
| WO | 97/48697 A1 | 12/1997 |
| WO | 98/08818 A1 | 3/1998 |
| WO | 99/18099 A1 | 4/1999 |
| WO | 99/28297 A1 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58511 A1 | 11/1999 |
| WO | 99/58519 A1 | 11/1999 |
| WO | 99/61435 A1 | 12/1999 |
| WO | 00/18764 A1 | 4/2000 |
| WO | 00/31036 A1 | 6/2000 |
| WO | 00/32180 A2 | 6/2000 |
| WO | 00/35919 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 01/53298 A1 | 7/2001 |
| WO | 01/77076 A1 | 10/2001 |
| WO | 01/83485 A1 | 11/2001 |
| WO | 02/30895 A1 | 4/2002 |
| WO | 02/36590 A1 | 5/2002 |
| WO | 02/072549 A1 | 9/2002 |
| WO | 03/000253 A1 | 1/2003 |
| WO | 03/000649 | 1/2003 |
| WO | 03/000671 | 1/2003 |
| WO | 03/000684 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |
| WO | 2005/030750 | 4/2005 |
| WO | 2005/030760 | 4/2005 |

OTHER PUBLICATIONS

Newman et al., "Solid-state analysis of the active pharmaceutical ingredient in drug products", DDT vol. 8, No. 19, Oct. 2003, p. 898-905.*

Iwaki et al., caplus an 1994:232264.*

Folkes et al., Bioorg. Med. Chem. Lett., 11 (2001) 2589-2592.*

Malamas, caplus an 1999:736673.*

Aggarwal et al., "A catalytic antibody programmed for torsional activation of amide bond hydrolysis," *Chem. Eur. J.*, Jan. 25, 2003, 9(13), 3132-3142.

Ballantine, J. A., "The Chemistry of Bacteria," *Journal of the Chemical Society Abstracts*, 1957, 2222-2227.

Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1422-1428.

Da Settimo, A. et al., "Reaction of indole derivatives with bromine, substitution, oxidation, and dimerization," J Org Chem, 1970, 35(8):2546-2551.

Delgado et al., Journal of Organic Chemistry (1993), 58(10), pp. 2862-2866.

Dillard R. D. et al.,."Indole Inhibitors of Human Nonpancreatic Secretory Phospholipase $A_2$ 1. Indole-3-Acetamides", *Journal of Medicinal Chemistry*, American Chemical Society, 39(26), 5119-5136.

Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.

Hipskind, P. A. et al., "Potent and selective 1,2,3-trisubstituted indole NPY Y-1 antagonists," *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9),1868-1873.

U.S. Appl. No. 10/947,711, filed Sep. 23, 2004, Gopalsamy et al.

Aznar, J. et al., "Role of Plasminogen Activator Inhibitor Type 1 in the Pathogenesis of Coronary Artery Diseases," *Haemostasis*, 24: 243-251 (1994).

Biemond, B. J. et al., "Thrombolysis and Reocclusion in Experimental Jugular Vein and Coronary Artery Thrombosis," *Circulation*, 91: 1175-1181 (1995).

Carmeliet, P. et al., "Plasminogen Activator Inhibitor -1 Gene-deficient Mice," *Journal of Clinical Investigation*, 92: 2756-2760 (Dec. 1993).

Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).

Hamsten, A. et. al., "Plasminogen Activator Inhibitor in Plasma: Risk Factor For Recurrent Myocardial Infarction," *Lancet*, 2: 3-9 (Jul. 4, 1987).

Juhan-Vague, I. et. al., "Deficient t-PA Release and Elevated PA Inhibitor Levels in Patients with Spontaneous or Recurrent Deep Venous Thrombosis," *Thromb Haemost*, 57: 67-72 (1987).

Juhan-Vague, I. et. al., "PAI-1, Obesity, Insulin Resistance and Risk of Cardiovascular Events," *Thromb Haemost*, 78: 656-660 (1997).

Koh, K. et. al., "Effects of Hormone-Replacement Therapy on Fibrinolysis in Postmenopausal Women," *N Engl J. Med*, 336(10): 683-690 (Mar. 6, 1997).

Krishnamurti, C. et al., "Plasminogen Activator Inhibitor: A Regulator of Ancrod-Induced Fibrin Deposition in Rabbits," *Blood*, 69(3): 798-803 (Mar. 1987).

Levi, M. et al., "Inhibition of Plasminogen Activator Inhibitor-1 Activity Results in Promotion of Endogenous Thrombolysis and Inhibition of Thrombus Extension in Models of Experimental Thrombosis," *Circulation*, 85, 305, (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).

Rocha, E. et al., "The Relationship Between Impaired Fibrinolysis and Coronary Heart Disease," *Fibrinolysis*, 8: 294-303 (1994).

Schneiderman, J. et. al., "Increased type 1 plasminogen activator inhibitor gene expression in atherosclerotic human arteries," *Proc Natl Acad Sci* 89: 6998-7002 (Aug. 1992).

Siemens, H. J. et. al., "Course of Molecular Hemostatic Markers During and After Different Surgical Procedures," *J Clin Anesthesia* 11: 622-629 (Dec. 1999).

* cited by examiner

THIAZOLO-NAPHTHYL ACIDS

CROSS-REFERENCE TO RELATED APPLICATIONS

This application claims priority to provisional application Ser. No. 60/603,739 filed on Aug. 23, 2004 incorporated herein by reference in its entirety.

BACKGROUND

The present invention relates generally to thiazolo-naphthyl acids and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main functions in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, Arteriosclerosis and Thrombosis, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for inhibitors of PAI-1 activity and methods of using them to modulate PAI-1 expression or activity, for example, in treating disorders associated with elevated PAI-1 levels.

SUMMARY

In one aspect, the present invention relates to thiazolo-naphthyl acids of the following formula:

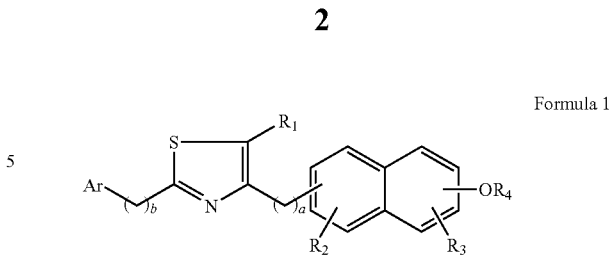

Formula 1 or a solvate, hydrate or pharmaceutically acceptable salt or ester form thereof; wherein:

Ar is aryl or heteroaryl;

$R_1$ is hydrogen, $C_1$-$C_{12}$ alkyl $C_{6-14}$ aryl, $C_{6-14}$ar($C_{1-6}$)alkyl, —($CH_2$)$_p$-heteroaryl, —($CH_2$)$_p$—CO-aryl, —($CH_2$)$_p$—CO-heteroaryl, —($CH_2$)$_p$—CO—($C_1$-$C_6$)alkyl, $C_2$-$C_7$ alkenyl, $C_2$-$C_7$ alkynyl, $C_3$-$C_8$ cycloalkyl, halogen, $C_1$-$C_3$ perfluoroalkyl, or $C_1$-$C_3$ perfluoroalkoxy;

$R_2$ and $R_3$ are independently hydrogen, $C_1$-$C_{12}$ alkyl, $C_{6-14}$ aryl, $C_{6-14}$ar($C_{1-6}$)alkyl, —($CH_2$)$_p$-heteroaryl, halogen, $C_1$-$C_3$ perfluoroalkyl, $C_1$-$C_3$perfluoroalkoxy, $C_1$-$C_6$ alkoxy, alkoxyaryl, nitro, carboxy($C_1$-$C_6$ alkyl), carbamide, carbamate, or $C_3$-$C_8$ cycloalkyl;

$R_4$ is —$CH(R_6)(CH_2)_nR_5$, —$C(CH_3)_2R_6$, —$CH(R_5)(CH_2)_n$ $R_6$, —$CH(R_5)C_6H_4R_6$, —$CH(R_5)C_6H_3(CO_2H)_2$, $CH(R_5)C_6H_2(CO_2H)_3$, or an acid mimic;

$R_5$ is hydrogen, $C_1$-$C_6$ alkyl, $C_6$-$C_{12}$ aryl, aralkyl, $C_3$-$C_8$ cycloalkyl, or —($CH_2$)$_n$($R_7$);

$R_6$ is $CO_2H$, tetrazole, or $PO_3H$;

$R_7$ is

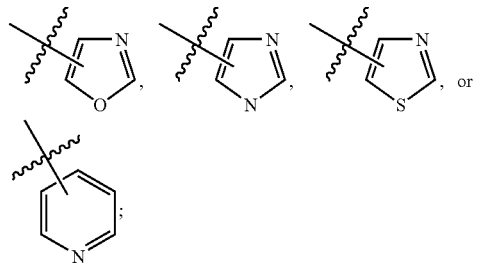

n is from 0 to 6;

p is from 0 to 3;

b is from 0 to 6; and a is from 0 to 6.

The present invention further provides, inter alia, methods of using thiazolo-naphthyl acids to, for example, modulate PAI-1 expression and/or activity. In certain methods, a therapeutically effective amount of one or more compounds of the present invention is administered to a subject to treat a PAI-1 related disorder. Exemplary methods are those that involve inhibiting PAI-1 activity in the subject, such as that associated with impairment of the fibrinolytic system. In certain embodiments, one or more compounds of the present invention is administered to a subject to treat thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds, for example, in medical therapies. Preferred compounds have properties that are useful for the prevention and/or inhibition, of a wide variety of diseases and disorders including those involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to about 12 carbon atoms, preferably 1 to about 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Accordingly, the alkyl groups described herein refer to both unsubstituted or substituted groups. Representative optional substituents include, but are not limited to, halogens, —CN, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, oxo (=O), and amino groups.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one double bond. Preferably, the alkenyl moiety has 1 or 2 double bonds. Preferably, the alkenyl moiety has about 2 to about 7 carbon atoms. Such alkenyl moieties can exist in the E or Z conformations and the compounds of this invention include both conformations. Specifically included within the definition of "alkenyl" are those aliphatic hydrocarbon chains that are optionally substituted. Accordingly, the alkenyl groups described herein refer to both unsubstituted or substituted groups. Representative optional substituents include, but are not limited to, halogens, —CN, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond. Preferred substituents include halogens, —CN, —OH, and amino groups.

The term "alkynyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one triple bond. Preferably, the alkynyl moiety has about 2 to about 7 carbon atoms. In certain embodiments, the alkynyl can contain more than one triple bond and, in such cases, the alkynyl group must contain at least four carbon atoms. Specifically included within the definition of "alkynyl" are those aliphatic hydrocarbon chains that are optionally substituted. Accordingly, the alkynyl groups described herein refer to both unsubstituted or substituted groups. Representative optional substituents include, but are not limited to, halogens, —CN, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, and amino groups. Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms (unless explicitly specified otherwise), preferably 3 to about 8 carbon atoms, more preferably 3 to about 6 carbon atoms. Specifically included within the definition of "cycloalkyl" are those alicyclic hydrocarbon groups that are optionally substituted. Accordingly, the cycloalkyl groups described herein refer to both unsubstituted or substituted groups. Representative optional substituents include, but are not limited to, halogens, —CN, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The term "aryl", as used herein, whether used alone or as part of another group, is defined as a substituted or unsubstituted aromatic hydrocarbon ring group having 5 to about 50 carbon atoms (unless explicitly specified otherwise) with from about 6 to about 14 carbon atoms being preferred, more preferably from about 6 to about 12 carbon atoms. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. Accordingly, the aryl groups (e.g., phenyl, naphthyl, and fluorenyl) described herein refer to both unsubstituted or substituted groups. In representative embodiments of the present invention, the "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, $C_3$-$C_6$ cycloalkyl, —$(CH_2)_p$—$C_3$-$C_6$ cycloalkyl, halogen, $C_1$-$C_3$ perfluoroalkyl, $C_1$-$C_3$ perfluoroalkoxy, —$(CH_2)_p$-phenyl, —$O(CH_2)_p$-phenyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. For example, the "aryl" groups can be optionally substituted with from 1 to 3 groups selected from $C_1$-$C_6$ alkyl, $C_1$-$C_6$ alkoxy, hydroxy, $C_3$-$C_6$ cycloalkyl, —$(CH_2)_p$-$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl. In these embodiments, the phenyl group of —$(CH_2)_p$-phenyl and —$O(CH_2)_p$-phenyl can be optionally substituted with, for example, from 1 to 3 groups selected from $C_1$-$C_6$ alkyl, $C_1$-$C_6$ alkoxy, —$(CH_2)_p$-phenyl phenyl, halogen, trifluoromethyl or trifluoromethoxy. P is an integer from 0 to 3. Preferred aryl groups include phenyl and naphthyl. Preferred substituents on the aryl groups herein include $C_1$-$C_6$ alkyl, $C_1$-$C_6$ alkoxy, halo, cyano, nitro, trihalomethyl, and $C_1$-$C_6$ thioalkoxy.

As used herein, the term "heteroaryl", whether used alone or as part of another group, is defined as a substituted or unsubstituted aromatic heterocyclic ring system. Heteroaryl groups can have, for example, from about 3 to about 50 carbon atoms (unless explicitly specified otherwise), with from about 4 to about 10 being preferred. In some embodiments, heteroaryl groups are aromatic heterocyclic ring systems having about 4 to about 14 ring atoms and containing carbon atoms and 1, 2, 3 or 4 oxygen, nitrogen or sulfur heteroatoms. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzothiophene, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic groups that are optionally substituted. Accordingly, the heteroaryl groups (e.g., furanyl, thienyl, benzofuranyl, benzothienyl, indolyl, pyrazolyl, and oxazolyl) described herein refer to both unsubstituted or substituted groups. In representative embodiments of the present invention, the "heteroaryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, $C_3$-$C_6$ cycloalkyl, —$(CH_2)_p$—$C_3$-$C_6$ cycloalkyl, $C_1$-$C_3$ perfluoroalkyl, $C_1$-$C_3$ perfluoroalkoxy, —$(CH_2)_p$-phenyl, —$O(CH_2)_p$-phenyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In some embodiments of the present invention, the "heteroaryl" groups can be optionally substituted with from 1 to 3 groups selected from $C_1$-$C_6$ alkyl, $C_1$-$C_6$ alkoxy, hydroxy, $C_3$-$C_6$ cycloalkyl, —$(CH_2)_p$-$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl. In these embodiments, the phenyl group of —$(CH_2)_p$-phenyl and —$O(CH_2)_p$-phenyl can be optionally substituted with from 1 to 3 groups selected from $C_1$-$C_6$ alkyl, $C_1$-$C_6$ alkoxy, phenyl, halogen, trifluoromethyl or trifluoromethoxy. P is an integer of from 0 to 3. Preferred heteroaryls of the present invention include substituted and unsubstituted furanyl, thienyl, benzofuranyl, benzothienyl, indolyl, pyrazolyl, and oxazolyl.

The term "alkoxy" as used herein, refers to the group $R_a$—O— wherein $R_a$ is an alkyl group as defined above. The term "thioalkoxy" as used herein, refers to the group —O—$R_a$—S wherein $R_a$ is an alkyl group as defined above. Specifically included within the definition of "alkoxy" and "thioalkoxy" are those groups that are optionally substituted. Preferred substituents on alkoxy and thioalkoxy groups include halogens, —CN, —OH, and amino groups.

The term "alkoxyaryl" as used herein, refers to the group $R_a$—O-aryl- wherein $R_a$ is an alkyl group as defined above and aryl is as defined above.

The term "arylalkyl" or "aralkyl" refers to the group —$R_a$-$R_b$, where $R_a$ is an alkylene group as defined above, substituted by $R_b$, an aryl group. Preferred aralkyl groups include $C_{6-14}$ar($C_{1-6}$)alkyl groups. Aralkyl groups of the present invention are optionally substituted. For example, in preferred embodiments, the benzyl groups of the present invention are optionally substituted with from 1 to 3 groups selected from $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl. Examples of arylalkyl moieties include, but are not limited to, benzyl, 1-phenylethyl, 2-phenylethyl, 3-phenylpropyl, 2-phenylpropyl and the like.

The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" or "halo" refers to chlorine, bromine, fluorine, and iodine.

The term "carbamide," as used herein, refers to the group —C(O)NR'R" where R' and R" are independently hydrogen, alkyl, aryl or cycloalkyl as defined herein.

The term "carbamate," as used herein, refers to the group —OC(O)NR'R" where R' and R" are independently hydrogen, alkyl, aryl or cycloalkyl as defined herein.

The term "acyl" refers to a radical of the formula RC(O)—, where R is hydrogen, alkyl, aryl, or cycloalkyl as defined herein. Suitable acyl radicals include formyl, acetyl, propionyl, and the like.

The term "acyloxy" refers to radicals of the formula RC(O)O—, where R is hydrogen, alkyl, aryl or cycloalkyl as defined herein. Suitable acyloxy radicals include $CH_3COO$—, $CH_3CH_2COO$—, benzoyloxy, and the like.

The term "acylamino" refers to radicals of the formula RC(O)NH— where R is hydrogen, alkyl, aryl, or cycloalkyl as defined herein.

The term "aminoacyl" refers to radicals of the formula —(R)$_{0-3}$(O)NH2 where R is alkylene as previously described.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder"

includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Methods known in the art for the detection of nucleic acids and proteins can be used for determining PAI-1 levels in a subject, e.g., PCR, northern and Southern blots, dot blots, nucleic acid arrays, western blots, immunoassays such as immunoprecipitation, ELISA, proteomics assays, and the like. Increased PAI-1 levels are indicative of disease.

In healthy individuals, PAI-1 is found at low levels in the plasma (for example, from about 5-26 ng/mL), but it is elevated significantly in a number of diseases, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following post-operative recovery from orthopedic surgery. (Siemens H J, et. al, *J Clin Anesthesia* 11: 622-629, 1999). Plasma PAI-1 is also elevated, for example, in post-menopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression include the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal subject is a subject not suffering from a PAI-1 related disorder or disease. In some embodiments of the present invention, the PAI-1 related disorder is not associated with hyperglycemia. A PAI-1 related disorder that is not associated with hyperglycemia is one, for example, that is not caused by elevated levels of glucose in the blood.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N-methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

The terms "inhibitors," "activators," and "modulators" as used in connection with expression or activity refer to inhibitory, activating, or modulating molecules, respectively. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means an amount that, when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention. In some embodiments of the present invention, the subject to be treated with the methods of the present invention does not have hyperglycemia and/or a disease that has been caused by hyperglycemia. Methods of determining whether a subject has hyperglycemia are known in the art and include, for example, performing a glucose test that measures the level of glucose in the blood. Two exemplary tests that can be used to measure the presence of excess levels of glucose in the blood include a test that measures the amount of glucose in the blood after an overnight fast and a test that measures the body's ability to process excess sugar presented after drinking a high glucose test. Typically a subject having a fasting sugar level (sugar level after an overnight fast) of about 64 to about 110 mg/dl does not have hyperglycemia whereas as person having a fasting sugar level of greater than 110 mg/dl has elevated blood sugar levels. A value above about 140 mg/dl on at least two occasions typically signifies that the subject has diabetes.

When any variable occurs more than one time in any constituent or in any formula, its definition in each occurrence is independent of its definition at every other occurrence. Combinations of substituents and/or variables are permissible only if such combinations result in stable compounds.

B. Thiazolo-Naphthyl Acids

As noted above, the compounds of the present invention include those of the following formula:

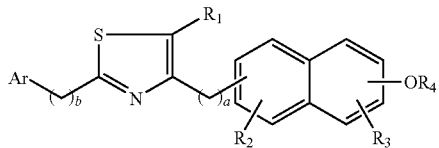

Formula 1 or solvates, hydrates or pharmaceutically acceptable salts or ester forms thereof; wherein:

Ar is aryl or heteroaryl;

$R_1$ is hydrogen, $C_1$-$C_{12}$ alkyl, $C_{6-14}$ aryl, $C_{6-14}$ar($C_{1-6}$)alkyl, —$(CH_2)_p$-heteroaryl, —$(CH_2)_p$—CO-aryl, —$(CH_2)_p$—CO-heteroaryl, —$(CH_2)_p$—CO—$(C_1$-$C_6)$alkyl, $C_2$-$C_7$ alkenyl, $C_2$-$C_7$ alkynyl, $C_3$-$C_8$ cycloalkyl, halogen, or $C_1$-$C_3$ perfluoroalkoxy;

$R_2$ and $R_3$ are independently hydrogen, $C_1$-$C_{12}$ alkyl, $C_{6-14}$ aryl, $C_{6-14}$ar($C_{1-6}$)alkyl, —$(CH_2)_p$-heteroaryl, halogen, $C_1$-$C_6$ alkoxy, alkoxyaryl, nitro, carboxy($C_1$-$C_6$ alkyl), carbamide, carbamate, or $C_3$-$C_8$ cycloalkyl;

$R_4$ is —$CH(R_6)(CH_2)_nR_5$, —$C(CH_3)_2R_6$, —$CH(R_5)(CH_2)_n R_6$, —$CH(R_5)C_6H_4R_6$, —$CH(R_5)C_6H_3(CO_2H)_2$, $CH(R_5)C_6H_2(CO_2H)_3$, or an acid mimic;

$R_5$ is hydrogen, $C_1$-$C_6$ alkyl, $C_6$-$C_{12}$ aryl, aralkyl, $C_3$-$C_8$ cycloalkyl, or —$(CH_2)_n(R_7)$;

$R_5$ is $CO_2H$, tetrazole, or $PO_3H$;

$R_7$ is

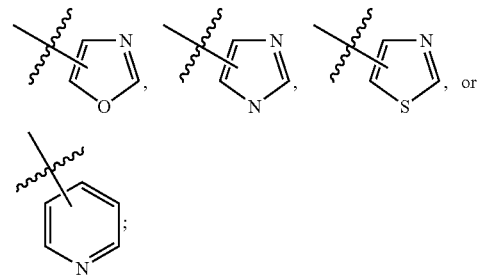

n is from 0 to 6;

p is from 0 to 3;

b is from 0 to 6; and a is from 0 to 6;

In certain embodiments, when b is from 1 to 6, Ar is phenyl, furanyl, thienyl, pyrazolyl, oxazolyl, or fluorenyl.

In certain embodiments in the definition of $R_1$, $R_2$ or $R_3$ said $C_1$-$C_{12}$ alkyl is $C_1$-$C_3$ perfluoroalkyl and said $C_1$-$C_6$ alkoxy is $C_1$-$C_3$ perfluoroalkoxy.

Thiazolo-naphthyl acids include the following compounds:

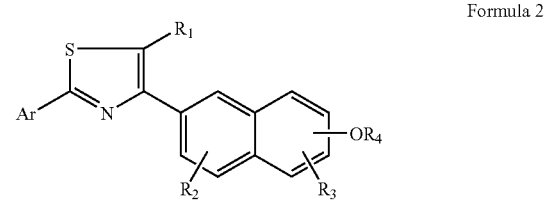

Formula 2

Formula 3

Formula 4

-continued

Formula 5

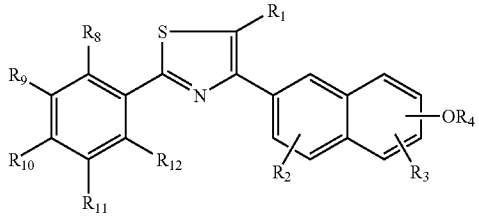

Formula 6

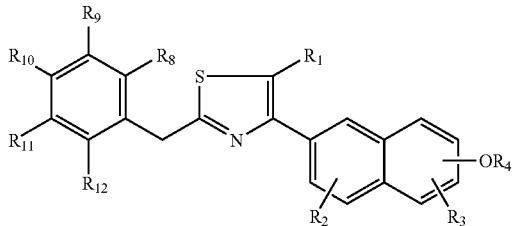

or solvates, hydrates or pharmaceutically acceptable salt or ester forms thereof; wherein Ar, $R_1$, $R_2$, $R_3$, $R_4$, b, n and p are as defined above and $R_8$, $R_9$, $R_{10}$, $R_{11}$ and $R_{12}$ are independently hydrogen, $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, —$(CH_2)_p$-phenyl, or —$O(CH_2)_p$-phenyl. In certain embodiments $C_1$-$C_6$ alkyl is $C_1$-$C_3$ perfluoroalkyl or said $C_1$-$C_6$ alkoxy is $C_1$-$C_3$ perfluoroalkoxy. In some exemplary compounds, $R_8$, $R_9$, $R_{10}$, $R_{11}$ and $R_{12}$ are independently hydrogen or halogen.

Exemplary compounds of Formulas 1 to 3 include those in which aryl is phenyl, naphthyl, furanyl, thienyl, benzofuranyl, benzothienyl, indolyl, pyrazolyl, oxazolyl or fluorenyl.

Exemplary compounds of Formulas 1 to 6 also include those in which:

$R_1$ is hydrogen, $C_1$-$C_6$ alkyl, $C_1$-$C_3$ perfluoroalkyl, halogen, or —$(CH_2)_p$-phenyl.

$R_2$ and $R_3$ are independently hydrogen, $C_1$-$C_6$ alkyl, phenyl-$(CH_2)_p$—, halogen or $C_1$-$C_3$ perfluoroalkyl.

$R_4$ is —$CHR_5CO_2H$, —$CH_2$-tetrazole or an acid mimic.

$R_5$ is hydrogen or optionally substituted benzyl.

Ar is phenyl, naphthyl, furanyl, thienyl, benzofuranyl, benzothienyl, indolyl, pyrazolyl, oxazolyl or fluorenyl or alternatively, Ar is phenyl, furanyl, thienyl, pyrazolyl, oxazolyl, or fluorenyl, or a solvate, hydrate or pharmaceutically acceptable salt or ester form thereof.

Exemplary compounds of Formulas 1 to 6 include those in which the definitions have one or more, e.g. all, of the following values:

$R_1$ is hydrogen or halogen;

$R_2$ and $R_3$ are independently hydrogen or halogen;

$R_4$ is —$CHR_5CO_2H$ or —$CH_2$-tetrazole;

$R_5$ is hydrogen or optionally substituted benzyl; and

Ar is unsubstituted phenyl or phenyl substituted with 1 to 3 groups selected from $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl.

In certain embodiments when b is from 1 to 6, Ar is phenyl, furanyl, thienyl, pyrazolyl, oxazolyl, or fluorenyl and when b is 0, Ar is furanyl, benzofuranyl, benzothienyl, indolyl, pyrazolyl, oxazolyl or fluorenyl.

Compounds of the present invention also include prodrugs and stereoisomers formulas 1-6.

In some embodiments of the present invention, $R_1$ is hydrogen, halogen, $C_1$-$C_{12}$ alkyl, $C_1$-$C_3$ perfluoroalkyl, or —$(CH_2)_p$-phenyl wherein the phenyl ring is optionally substituted with $C_1$-$C_6$ alkyl, $C_1$-$C_6$ alkoxy, halogen, trifluoromethyl, or trifluoromethoxy. In certain embodiments of the present invention, $R_1$ is hydrogen or halogen. For example, in some embodiments, $R_1$ is hydrogen or bromine.

In some compounds of the present invention, $R_2$ and $R_3$ are, independently, hydrogen, $C_1$-$C_{12}$ alkyl, halogen, $C_1$-$C_3$ perfluoroalkyl, or —$(CH_2)_p$-phenyl wherein the phenyl ring is optionally substituted with $C_1$-$C_6$ alkyl, $C_1$-$C_6$ alkoxy, halogen, trifluoromethyl, or trifluoromethoxy. In certain embodiments of the present invention, $R_2$ is hydrogen and $R_3$ is hydrogen or halogen. For example $R_3$ is hydrogen or bromine.

In some compounds, $R_4$ is —$CHR_5CO_2H$, —$CH_2$-tetrazole, —$CH(R_5)C_6H_4CO_2H$, $CH(R_5)C_6H_3(CO_2H)_2$ or an acid mimic. In certain embodiments, $R_4$ is unsubstituted $CH_2COOH$, substituted $CH_2COOH$, —$CH_2$-tetrazole or —$CH(R_5)C_6H_4CO_2H$. In some embodiments, for example $R_4$ is unsubstituted $CH_2COOH$; $CH_2COOH$ wherein the methylene group is substituted with benzyl; —$CH_2$-tetrazole; or —$CH(R_5)C_6H_4CO_2H$.

In some compounds of the present invention, the phenyl or benzyl groups of $R_5$ are optionally substituted with from 1 to 3 groups selected from $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl.

In some compounds, Ar is substituted or unsubstituted phenyl, naphthyl, furanyl, thienyl, benzofuranyl, benzothienyl, indolyl, pyrazolyl, oxazolyl or fluorenyl. In certain embodiments, Ar is a substituted or unsubstituted phenyl.

In some compounds of the present invention, the substituent $OR_4$ is in the 6 position relative to the thiazole ring (the numbering system used is shown in Formula 3).

Exemplary thiazolo-naphthyl acids of the present invention include, but are not limited to, 3-phenyl-2-{[6-(2-phenyl-1,3-thiazol-4-yl)-2-naphthyl]oxy}propanoic acid or a pharmaceutically acceptable salt or ester form thereof; 5-({[6-(2-phenyl-1,3-thiazol-4-yl)-2-naphthyl]oxy}methyl)-1H-tetraazole or a pharmaceutically acceptable salt or ester form thereof; 2-{[1-bromo-6-(2-phenyl-1,3-thiazol-4-yl)-2-naphthyl]oxy}-3-phenylpropanoic acid or a pharmaceutically acceptable salt or ester form thereof; {[1-bromo-6-(2-phenyl-1,3-thiazol-4-yl)-2-naphthyl]oxy}acetic acid or a pharmaceutically acceptable salt or ester form thereof; 5-({[1-bromo-6-(2-phenyl-1,3-thiazol-4-yl)-2-naphthyl]oxy}methyl)-1H-tetraazole or a pharmaceutically acceptable salt or ester form thereof; ({6-[2-(2,6-dichlorobenzyl)-1,3-thiazol-4-yl]-2-naphthyl}oxy)acetic acid or a pharmaceutically acceptable salt or ester form thereof; 2-{[1-bromo-6-(5-bromo-2-phenyl-1,3-thiazol-4-yl)-2-naphthyl]oxy}-3-phenylpropanoic acid or a pharmaceutically acceptable salt or ester form thereof; and 4-({[1-bromo-6-(2-phenyl-1,3-thiazol-4-yl)-2-naphthyl]oxy}methyl)benzoic acid or a pharmaceutically acceptable salt or ester form thereof.

The present invention also provides compositions comprising the thiazolo-naphthyl acids of the present invention, including those compounds of formulas 1-6 or a stereoisomer or pharmaceutically acceptable solvate, hydrate, salt or ester form thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more thiazolo-naphthyl acids.

Certain of the compounds of formulas 1-6 contain stereogenic carbon atoms or other chiral elements and thus give rise to stereoisomers, including enantiomers and diastereomers. The present invention includes all of the stereoisomers of formulas 1-6, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases or acids known in the art. The acids include, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hydroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms can be prepared using the acidic compound(s) of Formulas 1-6 and procedures known in the art.

Exemplary ester forms of the compounds of this invention include, but are not limited to, straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. Other exemplary esters include, but are not limited to, those of the formula —COOR$_{13}$ wherein R$_{13}$ is selected from the formula:

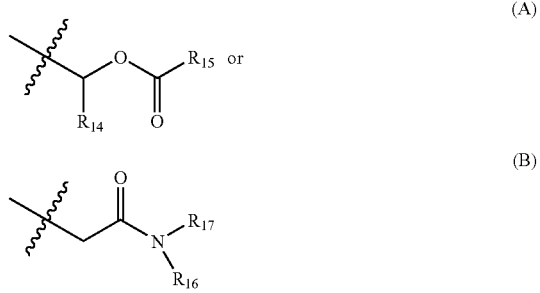

wherein R$_{14}$, R$_{15}$, R$_{16}$, and R$_{17}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, The Organic Chemistry of Drug Design and Drug Action, Academic Press (1992) and others. Exemplary acid mimics or mimetics include, but are not limited to, tetrazole, tetronic acid or groups having the formula:

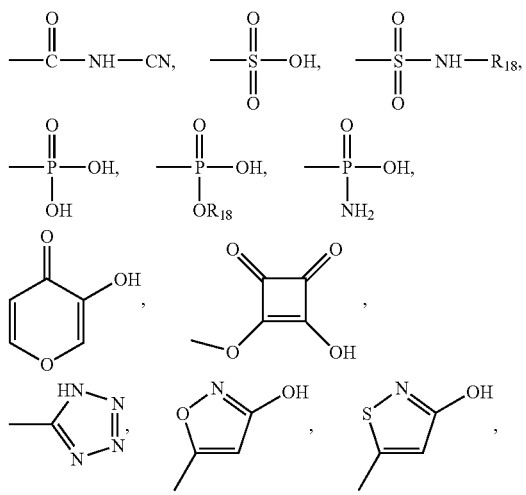

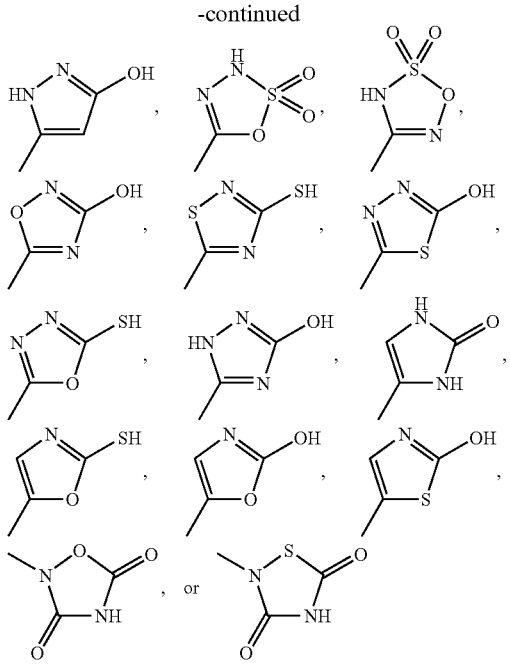

wherein $R_{18}$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$—($C_3$-$C_6$ cycloalkenyl), optionally substituted aryl or heteroaryl groups or optionally substituted -aryl($C_1$-$C_6$)alkyl or -heteroaryl($C_1$-$C_6$)alkyl, with the aryl and heteroaryl groups as defined herein.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer the compounds of the present invention, including those represented by formulas 1-6, to a subject suffering from any of the diseases associated with increased PAI-1 activity or expression, e.g., diabetes or cardiovascular disease, in order to effect treatment for that disease.

In one exemplary embodiment, the compounds of the present invention are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using the compounds of the present invention. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins.

The compounds of the present invention can be used to treat, for example, diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis Overview

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art. In the following reaction schemes, the substituents are selected from the groups defined above.

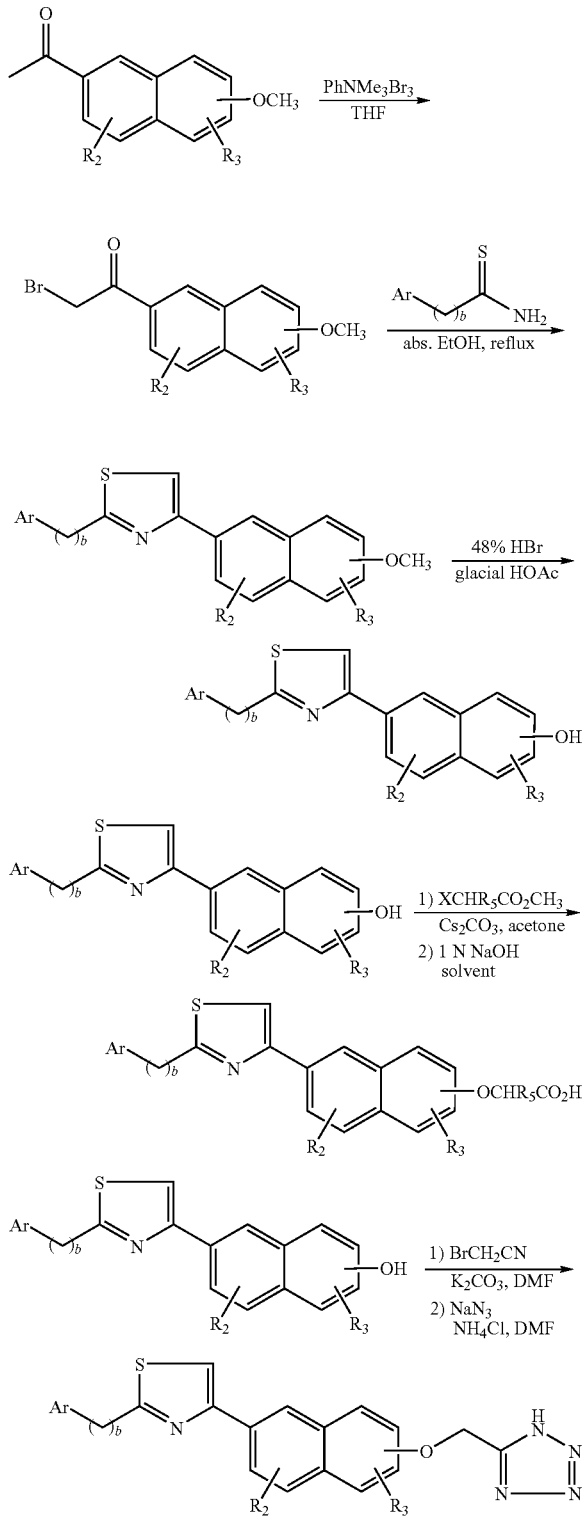

Scheme 1

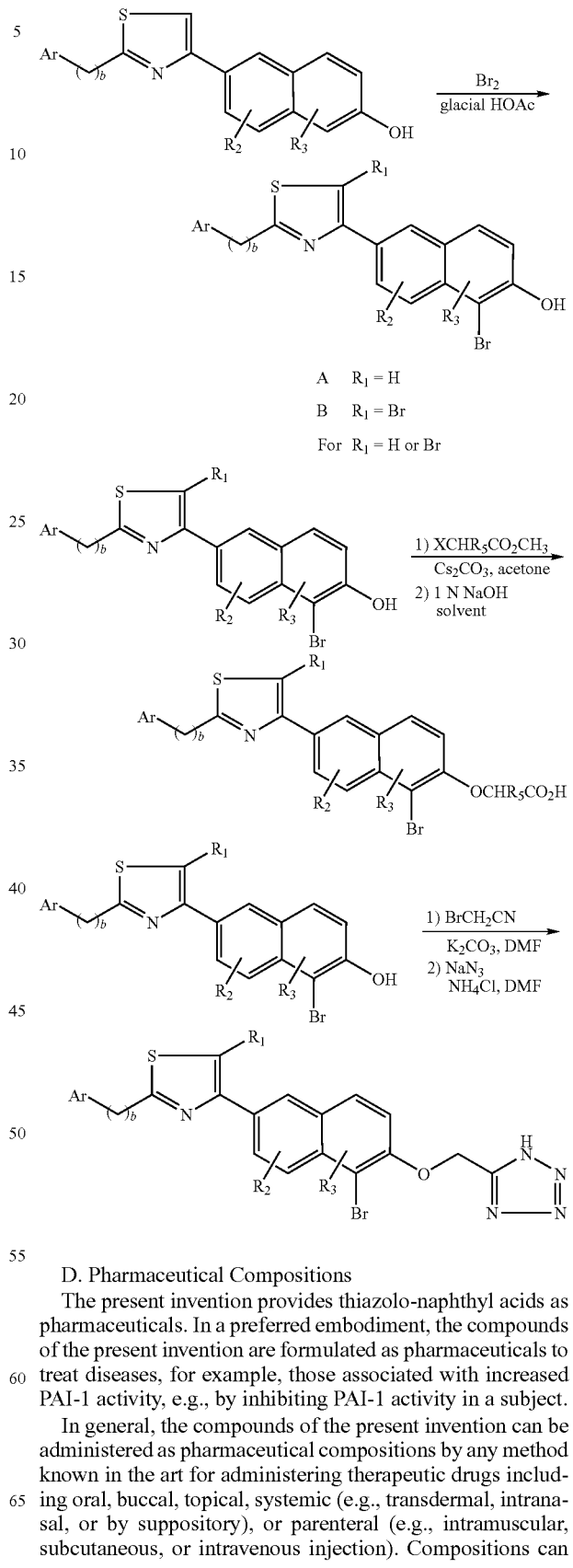

Scheme 2

A  $R_1 = H$
B  $R_1 = Br$

For $R_1 = H$ or Br

D. Pharmaceutical Compositions

The present invention provides thiazolo-naphthyl acids as pharmaceuticals. In a preferred embodiment, the compounds of the present invention are formulated as pharmaceuticals to treat diseases, for example, those associated with increased PAI-1 activity, e.g., by inhibiting PAI-1 activity in a subject.

In general, the compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, thiazolo-naphthyl acids suitable for use in the practice of this invention will be administered either singly or in combination with at least one other compound of this invention. Thiazolo-naphthyl acids suitable for use in the practice of the present invention can also be administered with at least one other conventional therapeutic agent for the disease being treated.

Aqueous suspensions of the invention can contain thiazolo-naphthyl acids in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a thiazolo-naphthyl acid in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of thiazolo-naphthyl acids in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Compounds suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise from, for example, 0.000001 percent by weight (% w) to 10% w of the compound, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art The compounds of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and a compound of the invention. In addition, these compositions can include other active agents, carriers, adjuvants, and the like.

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder in, for example, 1 mM-50 mM histidine, 0.1%-2% sucrose, 2%-7% mannitol at a pH range of 4.5 to 5.5, that is combined with buffer prior to use.

A pharmaceutical composition of the invention can optionally contain, in addition to a thiazolo-naphthyl acid, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration E. Determining Dosage Regimens For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathological assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day. In some embodiments, a daily dosage of from about 1 mg/kg to about 250 mg/kg is provided.

The compounds of the present invention can also be solvated, especially hydrated. Hydration can occur during manufacturing of the compounds or compositions comprising the compounds, or the hydration can occur over time due to the hygroscopic nature of the compounds.

In certain embodiments, the present invention is directed to prodrugs of compounds of formulas 1-6. The term "prodrug," as used herein, means a compound that is convertible in vivo by metabolic means (e.g. by hydrolysis) to a compound of formulas 1-6. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews,* 8:1-38 (1992), Bundgaard, *J. of Pharmaceutical Sciences,* 77:285 et seq. (1988); and Higuchi and Stella (eds.) Prodrugs as Novel Drug Delivery Systems, American Chemical Society (1975).

F. Kits

Pharmaceutical dosage forms comprising a compound of the present invention can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. For administration of pharmaceuticals comprising thiazolo-naphthyl acids, such labeling would include, for example, instructions concerning the amount, frequency and method of administration. Similarly, for administration of multiple pharmaceuticals provided in the container, such labeling would include, for example, instructions concerning the amount, frequency and method of administration of each dosage form.

EXAMPLES

Example 1

Synthesis of 3-phenyl-2-{[6-(2-phenyl-1,3-thiazol-4-yl)-2-naphthyl]oxy}propanoic acid Step 1: 2-Bromo-1-(6-methoxy-2-naphthyl)ethanone. Phenyltrimethylammoniun tribromide (9.45 g, 25.1 mmol) was added under nitrogen in portions over approximately 2 h to a solution of 1-(6-methoxy-naphthalen-2-yl)-ethanone (5.05 g, 25.2 mmol) in 50 mL of anhydrous THF at room temperature. After the addition the reaction was stirred at room temperature for 0.5 h. and then 250 mL of cold water was added. The solid present was collected by filtration, rinsed with 50 mL of water and dried under reduced pressure to give 6.66 g of a tan solid. Recrystallization of the solid from isopropyl alcohol gave 2-bromo-1-(6-methoxy-2-naphthyl) ethanone (4.07 g, 58%) as a brown solid, mp 109-112° C. Elemental Analysis for $C_{13}H_{11}BrO_2$ Calc'd: C, 55.94; H, 3.97; N, 0.00. Found: C, 56.03; H, 3.94; N, 0.00.

Step 2: 4-(6-methoxy-2-naphthyl)-2-phenyl-1,3-thiazole. Thiobenzamide (447 mg, 3.26 mmol) was added under nitrogen to a solution of (2-bromo-1-(6-methoxy-2-naphthyl) ethanone (906 mg, 3.25 mmol), prepared in the previous step, in 25 mL of absolute ethanol at approximately 70° C. After the addition the reaction was refluxed for 2 h. The solid was collected by filtration, rinsed with absolute ethanol and dried under reduced pressure to give 4-(6-methoxy-2-naphthyl)-2-phenyl-1,3-thiazole (909 mg, 88%) as a white solid, mp 191-193° C. Elemental Analysis for $C_{20}H_{15}NOS$ Calc'd: C, 75.68; H, 4.76; N, 4.41. Found: C, 75.37; H, 4.65; N, 4.31.

Step 3: 6-(2-phenyl-1,3-thiazol-4-yl)-2-naphthol. A solution of 4-(6-methoxy-2-naphthyl)-2-phenyl-1,3-thiazole (804 mg, 2.53 mmol), prepared in the previous step, in 50 mL of glacial HOAc plus 25 mL of 48% HBr was stirred under nitrogen at 120° C. for 3 h. The solvent was removed under reduced pressure and the residue partitioned between 10% methanol-methylene chloride and 5% NaHCO$_3$. (Note: The solid that did not dissolve in either layer was collected by filtration and saved as the HCL salt of the desired product). The aqueous layer was separated and extracted three times with 10% methanol-methylene chloride. The combined extracts were dried (MgSO$_4$), filtered and the solvent removed under reduced pressure to give 6-(2-phenyl-1,3-thiazol-4-yl)-2-naphthol (650 mg, 85%) as a brown solid, mp 194-197° C. Elemental Analysis for $C_{19}H_{13}NOS$ Calc'd: C, 75.22; H, 4.32; N, 4.62. Found: C, 74.22; H, 4.12; N, 4.43

Step 4: 2-Hydroxy-3-phenyl-propionic acid methyl ester. Hydrogen chloride was bubbled for 15 minutes into a solution of 2-hydroxy-3-phenyl-propionic acid (10.0 g, 60 mmol) in 100 mL of methanol at room temperature. The vessel was sealed and then stirred overnight at room temperature. The reaction was made basic by the addition of 5% NaHCO$_3$ and then concentrated under reduced pressure to remove the methanol. The residue was diluted with water and extracted with ethyl acetate. The organic layer was extracted with saturated NaCl, dried (MgSO$_4$), filtered and the solvent removed under reduced pressure to give 2-hydroxy-3-phenyl-propionic acid methyl ester (9.7 g, 90%) as a yellow oil, MS m/z 180 [M]$^+$. Elemental Analysis for $C_{10}H_{12}O_3$ Calc'd: C, 66.65; H, 6.71; N, 0.00. Found: C, 66.52; H, 6.86; N, 0.29

Step 5: 3-Phenyl-2-trifluoromethanesulfonyloxy-propionic acid methyl ester. Triethylamine (931 µL, 6.68 mmol) was added under nitrogen to a solution of 2-hydroxy-3-phenyl-propionic acid methyl ester (1.00 g, 5.57 mmol), prepared in the previous step, in 20 mL of chloroform (99.9%; free of ethanol) at dry ice-acetone temperature. Trifluoromethanesulfonic anhydride (1.03 mL, 6.13 mmol) was then added dropwise over 15 minutes. The cooling bath was removed and the reaction was stirred overnight at room temperature. The reaction was extracted with 1 N HCl, 5% NaHCO$_3$, dried (MgSO$_4$), filtered and the solvent removed under reduced pressure to give 1.53 g a brown oil. Purification of the oil on 100 g of silica gel (230-400 mesh) using 3:1 methylene chloride:hexane as the eluent gave 3-phenyl-2-trifluoromethanesulfonyloxy-propionic acid methyl ester (1.106 g, 64%) as clear oil. Elemental Analysis for $C_{11}H_{11}F_3O_5S$ Calc'd: C, 42.31; H, 3.55; N, 0.00. Found: C, 42.15; H, 3.35; N, 0.14

Step 6: Methyl 3-phenyl-2-{[6-(2-phenyl-1,3-thiazol-4-yl)-2-naphthyl]oxy} propanoate. A mixture of 6-(2-phenyl-1,3-thiazol-4-yl)-2-naphthol (247 mg, 0.814 mmol), prepared in step 3,3-phenyl-2-trifluoromethanesulfonyloxy-propionic acid methyl ester (387 mg, 1.24 mmol), prepared in the previous step, and cesium carbonate (532 mg, 1.63 mmol) in 20 mL of acetone was stirred under nitrogen at room temperature for 17 h. The reaction was concentrated under reduced pressure to remove the acetone. The residue was partitioned between methylene chloride and water. The aqueous layer was separated and extracted three times with methylene chloride. The combined extracts were dried (MgSO$_4$), filtered and the solvent removed under reduced pressure to give 449 mg of a brown oil. Purification of the oil on 300 g of silica gel (230-400 mesh) using 1:1 to 3:2 methylene chloride:hexane as the eluent gave methyl 3-phenyl-2-{[6-(2-phenyl-1,3-thiazol-4-yl)-2-naphthyl]oxy}propanoate (333 mg, 88%) as a white foam, MS (ESI) m/z 466 [M+H]$^+$. Elemental Analysis for $C_{29}H_{23}NO_3S$ Calc'd: C, 74.82; H, 4.98; N, 3.01. Found: C, 74.46; H, 4.96; N, 2.81.

Step 7: 3-Phenyl-2-{[6-(2-phenyl-1,3-thiazol-4-yl)-2-naphthyl]oxy}propanoic acid. A mixture of methyl 3-phenyl-2-{[6-(2-phenyl-1,3-thiazol-4-yl)-2-naphthyl]oxy} propanoate (260 mg, 0.559 mmol), prepared in the previous step, and 1 N NaOH (839 µL, 0.839 mmol) in 40 mL of THF plus 10 mL of water was refluxed under nitrogen for 3.5 h and then stood overnight at room temperature. By TLC starting material remained. An additional 559 µL (0.559 mmol) of 1 N NaOH was added and the mixture refluxed for 3 h. The reaction was acidified by the addition of 2 mL of 1 N HCl and then concentrated under reduced pressure to remove the THF. The gum present was dissolved in methylene chloride and the mixture concentrated under reduced pressure. The solid present was collected by filtration, rinsed with water and dried under reduced pressure to give the title compound (234 mg, 92%) as a yellow solid, mp 154-160° C. Elemental Analysis for $C_{28}H_{21}NO_3S+0.2H_2O$ Calc'd: C, 73.89; H, 4.74; N, 3.08. Found: C, 72.55; H, 4.99; N, 2.67

Example 2

Synthesis of 5-({[6-(2-phenyl-1,3-thiazol-4-yl)-2-naphthyl]oxy}methyl)-1H-tetraazole Step 1: {[6-(2-Phenyl-1,3-thiazol-4-yl)-2-naphthyl] oxy}acetonitrile. A mixture of 6-(2-phenyl-1,3-thiazol-4-yl)-2-naphthol (300 mg, 0.990 mmol), prepared in step 3 of Example 1, bromoacetonitrile (83 µL, 1.19 mmol) and potassium carbonate (684 mg, 4.95 mmol) in 15 mL of DMF was stirred under nitrogen at room temperature for 21 h. By TLC some starting material remained. An additional 34 µL (0.488 mmol) of bromoacetonitrile was added and the reaction stirred at room temperature for three days. The reaction was partitioned between ethyl acetate and water. The emulsion that formed was separated by the addition of saturated sodium chloride. The organic layer was separated, extracted multiple times with water, dried (MgSO$_4$), filtered and the solvent removed under reduced pressure to give 311 mg of a brown solid. Purification of the solid on 250 g of silica gel (230-400 mesh) using 1:1 to 3:2 methylene chloride:hexane as the eluents gave {[6-(2-phenyl-1,3-thiazol-4-yl)-2-naphthyl] oxy}acetonitrile (256 mg, 76%) as a white solid, mp 113-117° C. Elemental Analysis for $C_{21}H_{14}N_2OS$ Calc'd: C, 73.66; H, 4.12; N, 8.18. Found: C, 72.83; H, 4.18; N, 8.03

Step 2: 5-({[6-(2-Phenyl-1,3-thiazol-4-yl)-2-naphthyl] oxy}methyl)-1H-tetraazole. A mixture of {[6-(2-phenyl-1,3-thiazol-4-yl)-2-naphthyl]oxy}acetonitrile (204 mg, 0.596 mmol), prepared in the previous step, sodium azide (119 mg, 1.82 mmol) and ammonium chloride (98 mg, 1.82 mmol) in 10 mL of DMF was stirred under nitrogen at 100° C. for 5 h. The reaction was partitioned between 10% methanol-methylene chloride and 1 N HCl. The organic layer was separated, extracted three times with water, dried (MgSO$_4$), filtered and the solvent removed under reduced pressure to give the title compound (87 mg, 37%) as a white solid, mp 226-228° C. Elemental Analysis for $C_{21}H_{15}N_5OS+0.23 H_2O$ Calc'd: C, 64.74; H, 4.00; N, 17.98. Found: C, 63.46; H, 4.08; N, 16.95

Example 3

Synthesis of 2-{[1-bromo-6-(2-phenyl-1,3-thiazol-4-yl)-2-naphthyl]oxy}-3-phenylpropanoic acid Step 1: 1-Bromo-6-(2-phenyl-1,3-thiazol-4-yl)-2-naphthol. Bromine (547 µL, 10.7 mmol) in 250 mL of glacial HOAc was added under nitrogen dropwise over approximately 7 h to a solution of 6-(2-phenyl-1,3-thiazol-4-yl)-2- naphthol (3.24 g, 10.7 mmol), prepared in step 3 of Example 1, in 600 mL of glacial HOAc at room temperature. After the addition the reaction was stirred at room temperature overnight. The solid was collected by filtration, rinsed with glacial HOAc and dried under reduced pressure to give 4.74 g of a yellow solid. The solid was dissolved in 500 ml of 20% methanol-methylene chloride and neutralized with 5% NaHCO$_3$. The aqueous layer was separated and extracted three times with 20% methanol-methylene chloride. The combined extracts were dried (MgSO$_4$), filtered and the solvent removed under reduced pressure to give 3.99 g of a light tan solid. Purification of the solid on 1 kg of silica gel (230-400 mesh) using 3:1 hexane:methylene chloride to 3:1 methylene chloride:hexane as the eluents gave 1-bromo-6-(2-phenyl-1,3-thiazol-4-yl)-2-naphthol (1.74 g, 43%) as a tan solid, mp 176-183° C. Elemental Analysis for C$_{19}$H$_{12}$BrNOS Calc'd: C, 59.70; H, 3.16; N, 3.66. Found: C, 59.16; H, 3.12; N, 3.48

Step 2: Methyl 2-{[1-bromo-6-(2-phenyl-1,3-thiazol-4-yl)-2-naphthyl]oxy}-3-phenylpropanoate. A mixture of 1-bromo-6-(2-phenyl-1,3-thiazol-4-yl)-2-naphthol (303 mg, 0.792 mmol), prepared in the previous step, 3-phenyl-2-trifluoromethanesulfonyloxy-propionic acid methyl ester (378 mg, 1.21 mmol), prepared in step 5 of Example 1, and cesium carbonate (517 mg, 1.59 mmol) in 25 mL of acetone was stirred under nitrogen at room temperature 18 h. The reaction was concentrated under reduced pressure to remove the acetone. The residue was partitioned between methylene chloride and water. The aqueous layer was separated and extracted three times with methylene chloride. The combined extracts were dried (MgSO$_4$), filtered and the solvent removed under reduced pressure to give 514 mg of a light yellow oil. Purification of the oil on 300 g of silica gel (230-400 mesh) using 3:2 to 1:1 hexane:methylene chloride as the eluents gave methyl 2-{[1-bromo-6-(2-phenyl-1,3-thiazol-4-yl)-2-naphthyl]oxy}-3-phenylpropanoate (372 mg, 86%) as an off-white solid, mp 96-101° C. Elemental analysis for C$_{29}$H$_{22}$BrNO$_3$S Calc'd: C, 63.97; H, 4.07; N, 2.57. Found: C, 63.87; H, 4.01; N, 2.44

Step 3: 2-{[1-bromo-6-(2-phenyl-1,3-thiazol-4-yl)-2-naphthyl]oxy}-3-phenylpropanoic acid. A mixture of methyl 2-{[1-bromo-6-(2-phenyl-1,3-thiazol-4-yl)-2-naphthyl]oxy}-3-phenylpropanoate (197 mg, 0.363 mmol), prepared in the previous step, and 1 N NaOH (544 µL, 0.544 mmol) in 20 mL of THF plus 20 mL of methanol plus 10 mL of water was refluxed under nitrogen for 3 h. The reaction was filtered, acidified by the addition of 2 mL of 1 N HCl and then concentrated under reduced pressure. The solid was collected by filtration, rinsed with water and dried under reduced pressure to give the title compound (178 mg, 92%) as a white solid, mp 220-224° C. Elemental Analysis for C$_{28}$H$_{20}$BrNO$_3$S+0.18H$_2$O Calc'd: C, 63.02; H, 3.85; N, 2.62. Found: C, 63.13; H, 3.70; N, 2.54.

Example 4

Synthesis of {[1-bromo-6-(2-phenyl-1,3-thiazol-4-yl)-2-naphthyl]oxy}acetic acid

Step 1: Methyl {[1-bromo-6-(2-phenyl-1,3-thiazol-4-yl)-2-naphthyl]oxy}acetate. A mixture of 1-bromo-6-(2-phenyl-1,3-thiazol-4-yl)-2-naphthol (356 mg, 0.931 mmol), prepared in step 1 of Example 3, methyl bromoacetate (106 µL, 1.12 mmol) and cesium carbonate (457 mg, 1.40 mmol) in 25 mL of acetone was stirred under nitrogen at room temperature for 19 h. The reaction was concentrated under reduced pressure to remove the acetone. The residue was partitioned between methylene chloride and water. The aqueous layer was separated and extracted multiple times with methylene chloride. The combined organic extracts were dried (MgSO$_4$), filtered and the solvent removed under reduced pressure to give methyl {[1-bromo-6-(2-phenyl-1,3-thiazol-4-yl)-2-naphthyl]oxy}acetate (401 mg, 95%) as an off-white solid, mp 156-159° C. Elemental Analysis for C$_{22}$H$_{16}$BrNO$_3$S Calc'd: C, 58.16; H, 3.55; N, 3.08. Found: C, 57.87; H, 3.43; N, 2.94.

Step 2: {[1-Bromo-6-(2-phenyl-1,3-thiazol-4-yl)-2-naphthyl]oxy}acetic acid. A mixture of methyl {[1-bromo-6-(2-phenyl-1,3-thiazol-4-yl)-2-naphthyl]oxy}acetate (217 mg, 0.477 mmol), prepared in the previous step, and 1 N NaOH (716 µL, 0.716 mmol) in 20 mL of THF plus 20 mL of methanol plus 10 mL of water was refluxed under nitrogen for 2.25 h. The reaction was filtered, acidified by the addition of 3 mL of 1 N HCl and then concentrated under reduced pressure. The solid that formed was collected by filtration, rinsed with water and dried under reduced pressure to give the title compound (195 mg, 92%) as a white solid, mp 222-230° C. Elemental Analysis for C$_{21}$H$_{14}$BrNO$_3$S+0.15H$_2$O Calc'd: C, 56.94; H, 3.25; N, 3.16. Found: C, 57.19; H, 3.18; N, 3.04.

Example 5

Synthesis of 5-({[1-bromo-6-(2-phenyl-1,3-thiazol-4-yl)-2-naphthyl]oxy}methyl)-1H-tetraazole Step 1: {[1-bromo-6-(2-phenyl-1,3-thiazol-4-yl)-2-naphthyl]oxy}acetonitrile. A mixture of 1-bromo-6-(2-phenyl-1,3-thiazol-4-yl)-2-naphthol (351 mg, 0.918 mmol), prepared in step 1 of Example 3, bromoacetonitrile (77 µL, 1.11 mmol) and cesium carbonate (1.505 g, 4.62 mmol) in 25 mL of acetone was stirred under nitrogen at room temperature for 19 h (overnight). The reaction was concentrated under reduced pressure to remove the acetone. The residue was partitioned between methylene chloride and water. The aqueous layer was separated and extracted three times with methylene chloride. The combined extracts were dried (MgSO$_4$), filtered and the solvent removed under reduced pressure to give {[1-bromo-6-(2-phenyl-1,3-thiazol-4-yl)-2-naphthyl]oxy}acetonitrile (382 mg, 99%) as a light tan solid, mp 157-160° C. Elemental Analysis for C$_{21}$H$_{13}$BrN$_2$OS Calc'd: C, 59.87; H, 3.11; N, 6.65. Found: C, 59.56; H, 3.28; N, 6.56.

Step 2: 5-({[1-bromo-6-(2-phenyl-1,3-thiazol-4-yl)-2-naphthyl]oxy}methyl)-1H-tetraazole. A mixture of {[1-bromo-6-(2-phenyl-1,3-thiazol-4-yl)-2-naphthyl]oxy}acetonitrile (277 mg, 0.658 mmol), prepared in the previous step, sodium azide (128 mg, 1.96 mmol) and ammonium chloride (110 mg, 2.05 mmol) in 15 mL of DMF was stirred under nitrogen at 100° C. for 4 h. The reaction was filtered and then 5 mL of 1 N HCl added to the filtrate followed by the addition of 20 mL of water. The solid present was collected by filtration, rinsed with water and dried under reduced pressure to give the title compound (276 mg, 82%) as an off-white solid, mp 227-231° C. Elemental Analysis for C$_{21}$H$_{14}$BrN$_5$OS+0.48 C$_3$H$_7$NO+0.47H$_2$O Calc'd: C, 53.07; H, 3.63; N, 15.11. Found: C, 53.08; H, 3.61; N, 14.91.

Example 6

Synthesis of ({6-[2-(2,6-dichlorobenzyl)-1,3-thiazol-4-yl]-2-naphthyl}oxy)acetic acid Step 1: 2-(2,6-Dichlorobenzyl)-4-(6-methoxy-2-naphthyl)-1,3-thiazole. A suspension of (2-bromo-1-(6-methoxy-2-naphthyl)ethanone (500 mg, 1.79 mmol), prepared in step 1 of Example 1, in 25 mL of absolute ethanol was heated under nitrogen to reflux temperature. At this point all of the solid had dissolved. At reflux temperature 2-(2,6-dichlorophenyl) ethanethioamide (395 mg, 1.79 mmol) was added and the reaction refluxed for 3 h. After cooling to room temperature the solid was collected by filtration, rinsed with absolute ethanol and dried under reduced pressure to give 575 mg of an off-white solid. The solid was dissolved in 20% methanol-methylene chloride. An excess of 5% $NaHCO_3$ was added to convert the amine salt to the free base. The aqueous layer was separated an extracted three times with 20% methanol-methylene chloride. The combined organic extracts were dried ($MgSO_4$), filtered and the solvent removed under reduced pressure to give 2-(2,6-dichlorobenzyl)-4-(6-methoxy-2naphthyl)-1,3-thiazole (432 mg, 60%) as a light tan solid, mp 136-138° C. Elemental Analysis for $C_{21}H_{15}Cl_2NOS$ Calc'd: C, 62.29; H, 3.76; N, 3.45. Found: C, 62.28; H, 3.67; N, 3.35.

Step 2: 6-[2-(2,6-Dichlorobenzyl)-1,3-thiazol-4-yl]-2-naphthol. A solution of 2-(2,6-dichlorobenzyl)-4-(6-methoxy-2-naphthyl)-1,3-thiazole (390 mg, 0.975 mmol), prepared in the previous step, in 50 mL of glacial HOAc plus 25 mL of 48% HBr was stirred under nitrogen at 120° C. for 3.5 h and then stood overnight at room temperature. The reaction was concentrated under reduced pressure. The residue was dissolved in 20% methanol-methylene chloride and neutralized with the addition of an excess of 5% $NaHCO_3$. The aqueous layer was separated and extracted three times with 20% methanol-methylene chloride. The combined extracts were dried ($MgSO_4$), filtered and the solvent removed under reduced pressure to give 6-[2-(2,6-dichlorobenzyl)-1,3-thiazol-4-yl]-2-naphthol (303 mg, 80%) as a brown solid, mp 191-193° C. Elemental Analysis for $C_{20}H_{13}Cl_2NOS$ Calc'd: C, 62.19; H, 3.39; N, 3.63. Found: C, 61.31; H, 3.30; N, 3.42.

Step 3: Methyl ({6-[2-(2,6-dichlorobenzyl)-1,3-thiazol-4-yl]-2-naphthyl}oxy)acetate. A mixture of 6-[2-(2,6-dichlorobenzyl)-1,3-thiazol-4-yl]-2-naphthol (269 mg, 0.696 mmol), prepared in the previous step, methyl bromoacetate (79 µL, 0.835 mmol) and cesium carbonate (341 mg, 1.05 mmol) in 25 mL of acetone was stirred under nitrogen at room temperature for 4 h. The reaction was concentrated under reduced pressure to remove the acetone. The residue was partitioned between methylene chloride and water. The aqueous layer was separated and extracted three times with methylene chloride. The combined extracts were dried ($MgSO_4$), filtered and the solvent removed under reduced pressure to give 298 mg of a tan solid. The solid was triturated multiple times with hexane and then dried under reduced pressure to give methyl ({6-[2-(2,6-dichlorobenzyl)-1,3-thiazol-4-yl]-2-naphthyl}oxy)acetate (298 mg, 93%) as a tan solid, mp 174-177° C. Elemental Analysis for $C_{23}H_{17}Cl_2NO_3S$ Calc'd: C, 60.27; H, 3.74; N, 3.06. Found: C, 59.03; H, 3.70; N, 2.88.

Step 4: ({6-[2-(2,6-Dichlorobenzyl)-1,3-thiazol-4-yl]-2-naphthyl}oxy)acetic acid. A mixture of methyl ({6-[2-(2,6-dichlorobenzyl)-1,3-thiazol-4-yl]-2-naphthyl}oxy)acetate (205 mg, 0.447 mmol), prepared in the previous step, and 1 N NaOH (671 µL, 0.671 mmol) in 20 mL of THF plus 20 mL of methanol plus 10 mL of water was refluxed under nitrogen for 2.5 h. The reaction was filtered, acidified by the addition of 3 mL of 1 N HCl and then concentrated under reduced pressure to remove the THF and methanol. The solid present was collected by filtration, rinsed with water and dried under reduced pressure to give the title compound (150 mg, 74%) as an off-white solid, mp 205-207° C. Elemental Analysis for $C_{22}H_{15}Cl_2NO_3S+0.30H_2O$ Calc'd: C, 58.75; H, 3.50; N, 3.11. Found: C, 59.09; H, 3.58; N, 2.92.

Example 7

Synthesis of 2-{[1-bromo-6-(5-bromo-2-phenyl-1,3-thiazol-4-yl)-2-naphthyl]oxy}-3-phenylpropanoic acid Step 1: 1-Bromo-6-(5-bromo-2-phenyl-1,3-thiazol-4-yl)-2-naphthol. Bromine (547 µL, 10.7 mmol) in 250 mL of glacial HOAc was added under nitrogen dropwise over approximately 7 h to a solution of 6-(2-phenyl-1,3-thiazol-4-yl)-2-naphthol (3.24 g, 10.7 mmol), prepared in step 3 of Example 1, in 600 mL of glacial HOAc at room temperature. After the addition the reaction was stirred at room temperature overnight. The solid was collected by filtration, rinsed with glacial HOAc and dried under reduced pressure to give 4.74 g of a yellow solid. The solid was dissolved in 500 mL of 20% methanol-methylene chloride and neutralized with 5% $NaHCO_3$. The aqueous layer was separated and extracted three times with 20% methanol-methylene chloride. The combined extracts were dried ($MgSO_4$), filtered and the solvent removed under reduced pressure to give 3.99 g of a light tan solid. Purification of the solid on 1 kg of silica gel (230-400 mesh) using 3:1 hexane:methylene chloride to 3:1 methylene chloride:hexane as the eluents gave 1-bromo-6-(5-bromo-2-phenyl-1,3-thiazol-4-yl)-2-naphthol (178 mg, 4%) as an off-white solid, mp 198-200° C. Elemental Analysis for $C_{19}H_{11}Br_2NOS$ Calc'd: C, 49.48; H, 2.40; N, 3.04. Found: C, 49.83; H, 2.36; N, 2.81

Step 2: Methyl 2-{[1-bromo-6-(5-bromo-2-phenyl-1,3-thiazol-4-yl)-2-naphthyl]oxy}-3-phenylpropanoate. A mixture of 1-bromo-6-(5-bromo-2-phenyl-1,3-thiazol-4-yl)-2-naphthol (132 mg, 0.286 mmol), prepared in the previous step, 3-phenyl-2-trifluoromethanesulfonyloxy-propionic acid methyl ester (136 mg, 0.435 mmol), prepared in step 5 of Example 1, and cesium carbonate (188 mg, 0.577 mmol) in 15 mL of acetone was stirred under nitrogen at room temperature 19.5 h. By TLC starting material remained. An additional 43.8 mg (0.140 mmol) of 3-phenyl-2-trifluoromethanesulfonyloxy-propionic acid methyl ester was added and the reaction stirred at room temperature for 6 h. The reaction was concentrated under reduced pressure to remove the acetone. The residue was partitioned between methylene chloride and water. The aqueous layer was separated and extracted three times with methylene chloride. The combined extracts were dried ($MgSO_4$), filtered and the solvent removed under reduced pressure to give 235 mg of a yellow oil. Purification of the oil on silica gel (230-400 mesh) using 3:2 hexane:methylene chloride as the eluent gave methyl 2-{[1-bromo-6-(5-bromo-2-phenyl-1,3-thiazol-4-yl)-2-naphthyl]oxy}-3-phenylpropanoate (125 mg, 70%) as a yellow foam, MS (ESI) m/z 622/624/626 [M+H]$^+$. Elemental Analysis for $C_{29}H_{21}Br_2NO_3S$ Calc'd: C, 55.88; H, 3.40; N, 2.25. Found: C, 56.33; H, 3.33; N, 2.14.

Step 3: 2-{[1-Bromo-6-(5-bromo-2-phenyl-1,3-thiazol-4-yl)-2-naphthyl]oxy}-3-phenylpropanoic acid. A mixture of methyl 2-{[1-bromo-6-(5-bromo-2-phenyl-1,3-thiazol-4-yl)-2-naphthyl]oxy}-3-phenylpropanoate (134 mg, 0.215 mmol), prepared in the previous step, and 1 N NaOH (323 µL, 0.323 mmol) in 10 mL of THF plus 10 mL of methanol plus 5 mL of water was refluxed under nitrogen 2 h. The reaction was filtered, acidified with 1 N HCl and then concentrated under reduced pressure to remove the THF and methanol. The solid present was collected by filtration, rinsed with water and dried under reduced pressure to give the title compound (68 mg, 52%) as a yellow solid, mp 221-223° C. Elemental Analysis for $C_{28}H_{19}Br_2NO_3S$ Calc'd: C, 55.19; H, 3.14; N, 2.30. Found: C, 56.17; H, 3.45; N, 2.05.

Example 8

Synthesis of 4-({[1-bromo-6-(2-phenyl-1,3-thiazol-4-yl)-2-naphthyl]oxy}methyl)benzoic acid Step 1: Methyl 4-({[1-bromo-6-(2-phenyl-1,3-thiazol-4-yl)-2-naphthyl]oxy}methyl)benzoate. A mixture of 1-bromo-6-(2-phenyl-1,3-thiazol-4-yl)-2-naphthol (0.43 g, 1.12 mmol), prepared in step 1 of Example 3, methyl 4-(bromomethyl)benzoate (259.7 mg, 1.13 mmol) and cesium carbonate (551.9 mg, 1.69 mmol) in 25 mL of acetone was stirred under nitrogen at room temperature for 18 h. The reaction was concentrated under reduced pressure to remove the acetone. The reaction was partitioned between methylene chloride and water. The aqueous layer was separated and extracted three times with methylene chloride. The combined extracts were dried ($MgSO_4$), filtered and the solvent removed under reduced pressure to give 514.0 mg of a yellow solid. Purification of the solid on 300 g of silica gel (230-400 mesh) using 2:1 hexane:methylene chloride to 3:2 methylene chloride:hexane as the eluents gave methyl 4-({[1-bromo-6-(2-phenyl-1,3-thiazol-4-yl)-2-naphthyl]oxy}methyl)benzoate (423.7 mg, 71%) as a white solid, mp 173-175° C. Elemental Analysis for $C_{28}H_{20}BrNO_3S$ Calc'd: C, 63.40; H, 3.80; N, 2.64. Found: C, 62.99; H, 4.15; N, 2.50.

Step 2: 4-({[1-bromo-6-(2-phenyl-1,3-thiazol-4-yl)-2-naphthyl]oxy}methyl)benzoic acid. A mixture of methyl 4-({[1-bromo-6-(2-phenyl-1,3-thiazol-4-yl)-2-naphthyl]oxy}methyl)benzoate (214.8 mg, 0.405 mmol), prepared in the previous step, and 1 N NaOH (608 µL, 0.608 mmol) in 40 mL of THF plus 40 mL of methanol plus 10 mL of water was refluxed for 24 h. By TLC starting material remained. An additional 608 µL (0.608 mmol) of 1 N NaOH was added and the mixture refluxed for 24 h. After cooling to room temperature the reaction was filtered, acidified by the addition of 5 mL of 1 N HCl and then concentrated under reduced pressure to remove the THF and methanol. The solid present was collected by filtration, washed with water and dried under reduced pressure to give the title compound (152.9 mg, 73%) as a white solid, mp 268-270° C. Elemental analysis for $C_{27}H_{18}BrNO_3S \cdot 0.20H_2O$ Calc'd: C, 62.36; H, 3.57; N, 2.69. Found: C, 62.38; H, 3.54; N, 2.62.

Example 9

Primary Screen for the PAI-1 Inhibition

Test compounds are dissolved in DMSO at a final concentration of 10 mM, then diluted 100× in physiologic buffer. The inhibitory assay is initiated by the addition of the test compound (1-100 µM final concentration, maximun DMSO concentration of 0.2%) in a pH 6.6 buffer containing 140 nM recombinant human plasminogen activator inhibitor-1 (PAI-1; *Molecular Innovations*, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the test compound on tPA alone.

Example 10

Assay for Determining $IC_{50}$ of Inhibition of PAI-1

This assay is based upon the non-SDS dissociable interaction between tPA and active PAI-1. Assay plates are initially coated with human tPA (10 µg/ml). Test compounds of the present invention are dissolved in DMSO at 10 mM, then diluted with physiologic buffer (pH 7.5) to a final concentration of 1-50 µM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the thiazolo-naphthyl acid/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405\ nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0-100 ng/ml.

The compound of the present invention inhibited Plasminogen Activator Inhibitor-1 as summarized in Table 1.

TABLE I

| Example | $IC_{50}$ (Antibody)[a] µM | % Inhibition 25 µM | % Inhibition 10 µM |
|---|---|---|---|
| 1 | 26.2 | 62 | 4 |
| 2 | 34.3 | 59 | 6 |
| 3 |  | 49 | 1 |
| 4 | 20.26 | 68 | 40 |
| 5 |  | 64 | 42 |
| 6 |  | 43 | 21 |
| 7 |  | 71 | 20 |
| 8 |  | 49 | 38 |

[a]The $IC_{50}$ was determined by the Antibody Assay as described above.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed is:

1. A compound of formula 1:

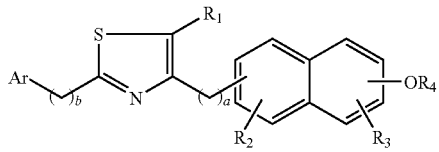

Formula 1 or pharmaceutically acceptable salt or ester form thereof; wherein:
Ar is phenyl;
$R_1$ is hydrogen, $C_1$-$C_{12}$ alkyl, —$(CH_2)_p$—CO—$(C_1$-$C_6)$ alkyl, $C_2$-$C_7$ alkenyl, $C_2$-$C_7$ alkynyl, halogen, or $C_1$-$C_3$ perfluoroalkoxy;
$R_2$ and $R_3$ are independently hydrogen, $C_1$-$C_{12}$ alkyl, halogen, $C_1$-$C_6$ alkoxy, nitro, carboxy($C_1$-$C_6$ alkyl), carbamide, carbamate;
$R_4$ is —$CH(R_6)(CH_2)_n R_5$, —$C(CH_3)_2 R_6$, —$CH(R_5)(CH_2)_n$ $R_6$, —$CH(R_5)C_6H_4R_6$, —$CH(R_5)C_6H_3(CO_2H)_2$, $CH(R_5)C_6H_2(CO_2H)_3$,
$R_5$ is hydrogen, $C_1$-$C_6$ alkyl, $C_6$-$C_{12}$ aryl, aralkyl, $C_3$-$C_8$ cycloalkyl, or —$(CH_2)_n(R_7)$;
$R_6$ is $CO_2H$, tetrazole, or $PO_3H$;
$R_7$ is

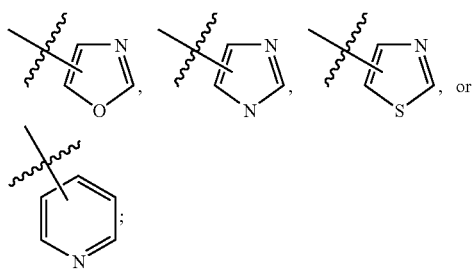

n is from 0 to 6;
p is from 0 to 3;
b is from 0 to 6; and
a is from 0 to 6.

2. The compound of claim 1, wherein said $C_{1-12}$ alkyl in $R_1$, $R_2$ and $R_3$ is unsubstituted or optionally substituted with halogen and said $C_{1-6}$ alkoxy is unsubstituted or optionally substituted with halogen.

3. The compound of claim 2 wherein said $C_{1-12}$ alkyl is unsubstituted $C_{1-12}$ alkyl or $C_{1-3}$ perfluoroalkyl and said $C_{1-6}$ alkoxy is unsubstituted $C_{1-6}$ alkoxy or $C_{1-3}$ perfluoroalkoxy.

4. The compound of claim 1 wherein
Ar is phenyl;
$R_1$ is hydrogen, halogen or $C_1$-$C_6$ alkyl;
$R_2$ and $R_3$ are independently hydrogen, $C_1$-$C_6$ alkyl, or halogen;
$R_4$ is —$CHR_5CO_2H$, —$CH_2$-tetrazole, —$CH(R_5)C_6H_4CO_2H$;
$R_5$ is hydrogen or benzyl; and
p is from 0 to 3;
or pharmaceutically acceptable salt or ester form thereof.

5. The compound of claim 4 wherein said $C_1$-$C_6$ alkyl is $R_1$, $R_2$ and $R_3$ is unsubstituted $C_1$-$C_6$ alkyl or $C_1$-$C_3$ perfluoroalkyl and the ring of said benzyl group in $R_5$ is unsubstituted or substituted with from 1 to 3 groups selected from the group consisting of $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, $C_1$-$C_3$ perfluoroalkyl, $C_1$-$C_3$ perfluoroalkoxy, —$(CH_2)_p$-phenyl, and —$O(CH_2)_p$-phenyl.

6. The compound of claim 4 having formula 2:

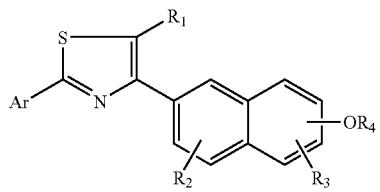

Formula 2 or pharmaceutically acceptable salt or ester form thereof.

7. The compound of claim 6 wherein $R_4$ is —$CHR_5CO_2H$, —$CH_2$-tetrazole, or $CH(R_5)C_6H_4CO_2H$.

8. The compound of claim 4 having formula 3:

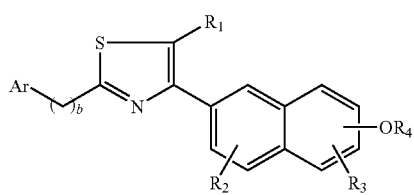

Formula 3 or pharmaceutically acceptable salt or ester form thereof.

9. The compound of claim 8 wherein $R_4$ is —$CHR_5CO_2H$, —$CH_2$-tetrazole, or $CH(R_5)C_6H_4CO_2H$.

10. The compound of claim 4 having formula 5:

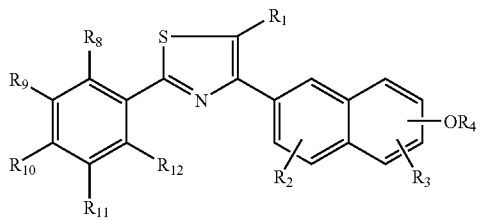

Formula 5 or pharmaceutically acceptable salt or ester form thereof wherein $R_8$, $R_9$, $R_{10}$, $R_{11}$ and $R_{12}$ are independently hydrogen, $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, —$(CH_2)_p$-phenyl, or —$O(CH_2)_p$-phenyl.

11. The compound of claim 10 wherein said $C_1$-$C_6$ alkyl is unsubstituted $C_1$-$C_6$ alkyl or $C_1$-$C_3$ perfluoroalkyl and $C_1$-$C_6$ alkoxy is unsubstituted $C_1$-$C_6$ alkoxy or $C_1$-$C_3$ perfluoroalkoxy.

12. The compound of claim 10 wherein $R_4$ is —$CHR_5CO_2H$, —$CH_2$-tetrazole, or $CH(R_5)C_6H_4CO_2H$.

13. The compound of claim 10 wherein $R_1$ is hydrogen.

14. The compound of claim 4 having formula 6:

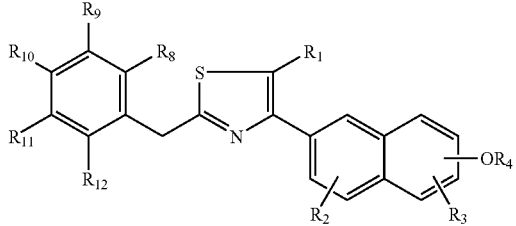

Formula 6 or pharmaceutically acceptable salt or ester form thereof wherein $R_8$, $R_9$, $R_{10}$, $R_{11}$ and $R_{12}$ are independently hydrogen, $C_1$-$C_6$ alkyl, $C_1$-$C_6$ alkoxy, hydroxy, $C_3$-$C_6$ cycloalkyl, —$(CH_2)_p$—$C_3$-$C_6$ cycloalkyl, halogen, —$(CH_2)_p$-phenyl, or —$O(CH_2)_p$-phenyl.

15. The compound of claim 14 wherein said $C_1$-$C_6$ alkyl is unsubstituted $C_1$-$C_6$ alkyl or $C_1$-$C_3$ perfluoroalkyl and $C_1$-$C_6$ alkoxy is unsubstituted $C_1$-$C_6$ alkoxy or $C_1$-$C_3$ perfluoroalkoxy.

16. The compound of claim 14 wherein $R_4$ is —$CHR_5CO_2H$, —$CH_2$-tetrazole, or $CH(R_5)C_6H_4CO_2H$.

17. The compound of claim 1 that is 3-phenyl-2-{[6-(2-phenyl-1,3-thiazol-4-yl)-2-naphthyl]oxy}propanoic acid or a pharmaceutically acceptable salt or ester form thereof; 2-{[1-bromo-6-(2-phenyl-1,3-thiazol-4-yl)-2-naphthyl]oxy}-3-phenylpropanoic acid or a pharmaceutically acceptable salt or ester form thereof; {[1-bromo-6-(2-phenyl-1,3-thiazol-4-yl)-2-naphthyl]oxy}acetic acid or a pharmaceutically acceptable salt or ester form thereof; 5-({[6-(2-phenyl-1,3-thiazol-4-yl)-2-naphthyl]oxy}ethyl)-1H-tetraazole or a pharmaceutically acceptable salt or ester form thereof; or 5-({[1-bromo-6-(2-phenyl-1,3-thiazol-4-yl)-2-naphthyl]oxy}methyl)-1H-tetraazole or a pharmaceutically acceptable salt or ester form thereof.

18. The compound of claim 1 that is 2-{[1-bromo-6-(5-bromo-2-phenyl-1,3-thiazol-4-yl)-2-naphthyl]oxy}-3-phenylpropanoic acid or a pharmaceutically acceptable salt or ester form thereof; ({6-[2-(2,6-dichlorobenzyl)-1,3-thiazol-4-yl]-2-naphthyl}oxy)acetic acid or a pharmaceutically acceptable salt or ester form thereof; 4-({[1-bromo-6-(2-phenyl-1,3-thiazol-4-yl)-2-naphthyl]oxy}methyl)benzoic acid or a pharmaceutically acceptable salt or ester form thereof.

19. A pharmaceutical composition comprising a compound of claim 1, or a pharmaceutically acceptable salt or ester form thereof, and a pharmaceutically acceptable excipient or carrier.

* * * * *